United States Patent [19]

Hudrlik

[11] Patent Number: 5,411,529
[45] Date of Patent: May 2, 1995

[54] WAVEFORM DISCRIMINATOR FOR CARDIAC STIMULATION DEVICES

[75] Inventor: Terrence R. Hudrlik, Fridley, Minn.

[73] Assignee: Medtronic, Inc., Minneapolis, Minn.

[21] Appl. No.: 120,613

[22] Filed: Sep. 13, 1993

Related U.S. Application Data

[63] Continuation-in-part of Ser. No. 626,061, Dec. 12, 1990, Pat. No. 5,265,603, which is a continuation-in-part of Ser. No. 566,636, Aug. 10, 1990, abandoned.

[51] Int. Cl.$^6$ ............................................. A61N 1/362
[52] U.S. Cl. ............................................. 607/6; 607/28
[58] Field of Search ..................... 607/6, 7, 8, 11, 28

[56] References Cited

U.S. PATENT DOCUMENTS

| | | |
|---|---|---|
| 3,857,398 | 12/1974 | Rubin . |
| 4,375,817 | 8/1983 | Engle et al. . |
| 4,384,585 | 5/1983 | Zipes . |
| 4,407,287 | 10/1983 | Herpers . |
| 4,548,209 | 10/1985 | Wielders et al. . |
| 4,552,154 | 11/1985 | Hartlaub . |
| 4,590,944 | 5/1986 | Mann et al. . |
| 4,693,253 | 9/1987 | Adams . |
| 4,830,006 | 5/1989 | Haluska et al. . |
| 5,115,807 | 5/1992 | Pless et al. .................. 607/8 |
| 5,156,149 | 10/1992 | Hudrlik . |
| 5,193,535 | 3/1993 | Bardy et al. . |

*Primary Examiner*—William E. Kamm
*Assistant Examiner*—Scott M. Getzow
*Attorney, Agent, or Firm*—Reed A. Duthler; Harold Patton

[57] ABSTRACT

An apparatus for producing signals indicative of power levels of depolarizations of heart tissue, particularly adapted for use in an implantable antiarrhythmia device or an implantable pacemaker. The device distinguishes between the power level of sensed depolarization signals in order to distinguish between different types of depolarization waveforms. In particular, the measured power level of the sensed depolarizations may be employed to distinguish between normally conducted and ectopic beats, for use in controlling the operation of an implantable antiarrhythmia device such as an implantable pacemaker/cardioverter/defibrillator or for use in controlling the operation of a bradycardia pacemaker.

23 Claims, 5 Drawing Sheets

WAVEFORM DISCRIMINATOR FOR CARDIAC STIMULATION DEVICES

This application is a continuation-in-part of U.S. patent application Ser. No. 07/626,061, filed Dec. 12, 1990, now U.S. Pat. No. 5,265,603 which was a continuation in part of U.S. patent application No. 07/566,636, filed Aug. 10, 1990, abandoned.

BACKGROUND OF THE INVENTION

This invention relates to implantable cardiac stimulators and more particularly to a system for discriminating among cardiac depolarization waveform types, for use in cardiac pacers and anti-tachycardia devices.

In the context of a cardiac stimulator, it is often desirable to be able to distinguish between different types of depolarization waveforms. For example, it is desirable to know whether a ventricular depolarization represents a normally conducted depolarization or an ectopic depolarization (PVC or ventricular tachycardia depolarization). In the context of cardiac pacemakers, the time order of atrial and ventricular depolarizations has typically been employed to distinguish between normally conducted depolarizations and PVCs. For example, see U.S. Pat. No. 4,407,287, issued to Herpers et al. In the context of implantable cardioverters and defibrillators, waveform analysis of detected depolarizations has often been suggested for use in distinguishing among various types of depolarizations. For example, measurement of R-wave width is disclosed as early U.S. Pat. No. 3,857,398, issued to Rubin et al., in the context of an implantable defibrillator, with more sophisticated waveform analysis circuitry to distinguish normally conducted from ectopic beats disclosed in U.S. Pat. No. 4,552,154, issued to Hartlaub et al, both of which are incorporated herein by reference in their entireties.

SUMMARY OF THE INVENTION

The present invention is directed toward a simple analog discriminator for distinguishing different types of detected cardiac depolarizations. The discriminator of the present invention accomplishes this object by means of circuitry which provides a measurement corresponding to the power of the depolarization wavefront, in the area adjacent the sensing electrode of the device. The device provides a current measurement and a voltage measurement and combines the two measurements to derive a signal proportional to the power associated with the depolarization wavefront, as seen by the sensing electrode. In particular, the device employs the field density clamp (FDC) amplifier geometry described in the above cited patents and applications by Hudrlik to deliver current to a sensing electrode located adjacent heart tissue, in order to counteract the depolarization induced disturbances of the charge equilibrium in the area adjacent the electrode. The FDC amplifier produces a first output signal proportional to the current delivered through the sensing electrode and a differential amplifier produces a second output signal proportional to the voltage differential between the tissue contacting sensing electrode and a second electrode. The first and second signals are combined to derive a signal proportional to the power delivered to the sensing electrode in response to the passage of the depolarization wavefront.

The power signal so derived may be employed to distinguish among various types of depolarizations. In particular, the inventor has determined that in the context of a sensing electrode located in the right ventricle, the power level of the depolarization wavefront in the vicinity of the electrode is substantially greater for ectopic beats (in particular PVC's) than for normally conducted beats. Thus, the power level may be employed to distinguish between normal beats and ectopic beats (PVC's). In the particular embodiment disclosed, the FDC amplifier is also employed to detect the occurrence of a depolarization. The output signal from the FDC amplifier is used to define an interval during which the power signal is integrated, with the integrated signal compared to a sensing threshold, intended to discriminate between normally conducted beats and ectopic beats (PVCs).

BRIEF DESCRIPTION OF THE DRAWINGS

In the drawing, like reference numerals indicate corresponding structures throughout the several views in which.

DETAILED DESCRIPTION OF THE PREFERRED EMBODIMENT

Figure 1:
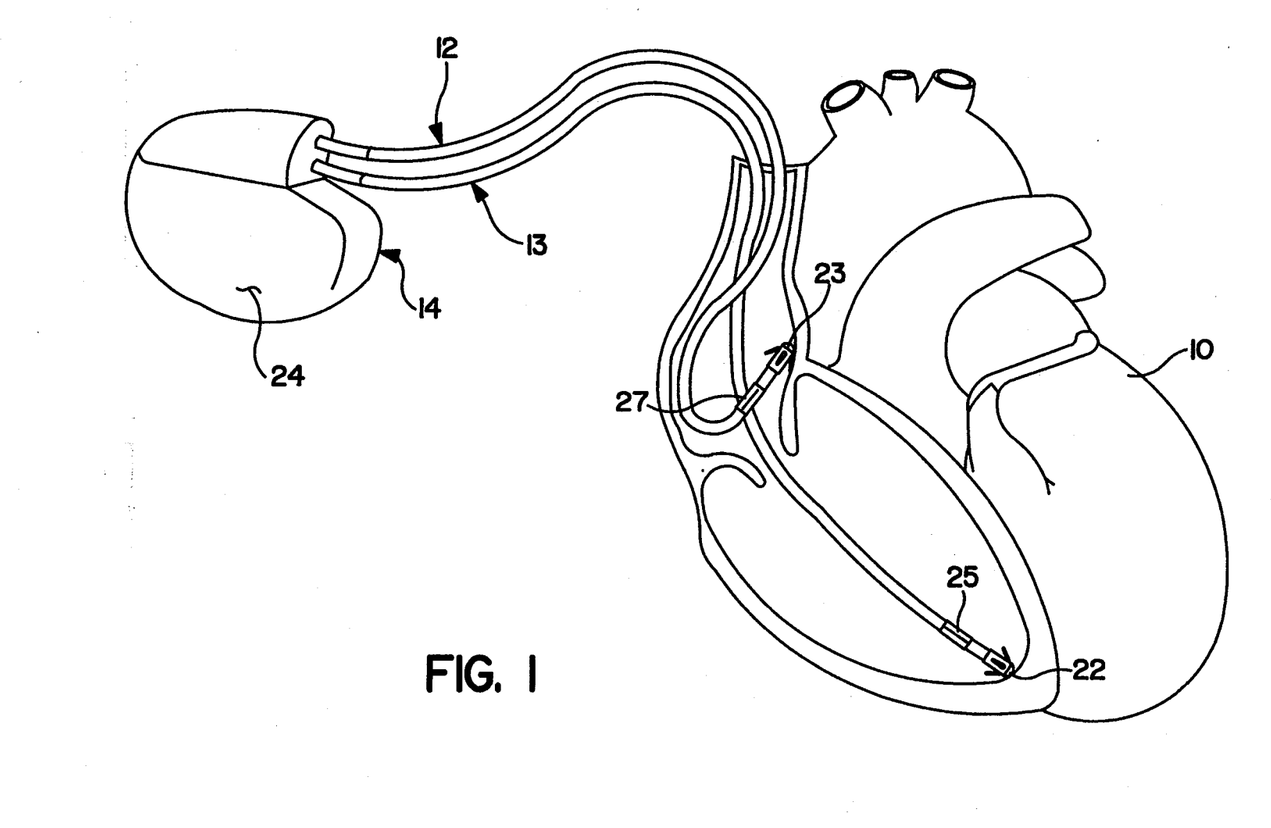
FIG. 1 is a diagram depicting the interconnection between an implantable pacemaker of a type in which the present invention may be practiced and the heart.

FIG. 1 illustrates an implanted dual chamber cardiac pacer. In the figure, the pacer 14 is implanted subcutaneously, between the skin and the ribs, located in the right pectoral region. Leads 12 and 13 are passed through a vein into the right ventricle and atrium, respectively, of the heart 10. The distal end of lead 12 has a tip electrode 22 contacting the interior of the ventricle. A second, ring electrode 25, is spaced from the tip electrode 22. The distal end of lead 13 similarly has a tip electrode 23 contacting the interior of the atrium and a ring electrode 27, is spaced from the tip electrode 23. Each of these electrodes is connected to the circuitry contained in the pacer 14. A portion of the metallic enclosure or "can" of the pacer may also optionally form an electrode surface 24.

Although a variety of lead configurations can be used to pace the heart and to sense the intrinsic depolarizations of the heart, the present invention is disclosed in a configuration where ventricular pacing is delivered using the tip electrode 22 and the ring electrode 25 and sensing is accomplished using the tip electrode 22 and the can electrode 24. Both sensing and pacing in the atrium are disclosed as accomplished using electrodes 23 and 27.

Figure 2:
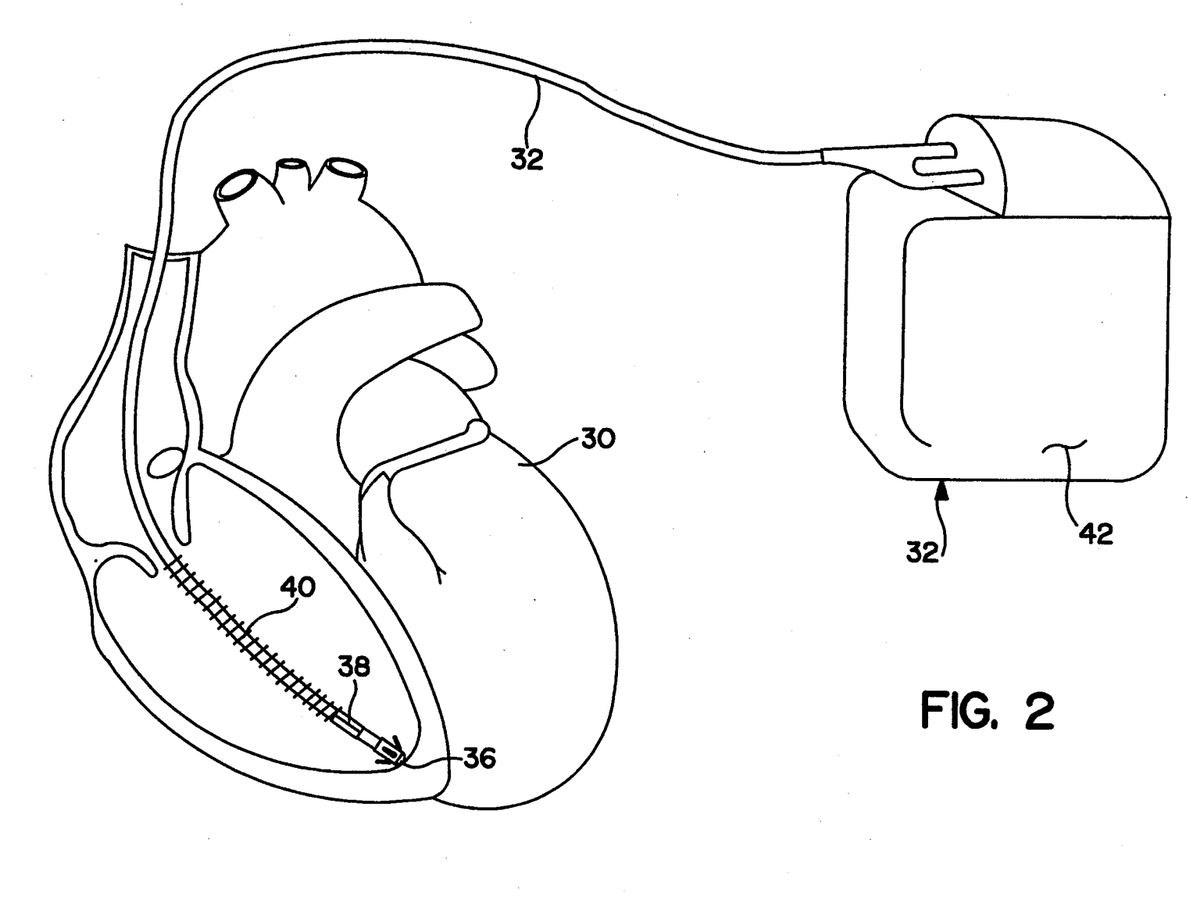
FIG. 2 is a diagram depicting the interconnection between an implantable defibrillator of a type in which the present invention may be practiced and the heart.

FIG. 2 illustrates an implanted ventricular pacemaker/cardioverter/ defibrillator. In the figure, the defibrillator 32 is implanted subcutaneously, between the skin and the ribs, located in the left pectoral region.

Lead 34 is passed through a vein into the right ventricle of the heart 30. The distal end of lead 34 has a tip electrode 36 contacting the interior of the ventricle. A second, ring electrode 38, is spaced from the tip electrode 36. An elongated defibrillation electrode 40 is located proximal to ring electrode 38, and extends to approximately the region of the tricuspid valve. Each of these electrodes is connected to the circuitry contained in the pacer 14. The metallic enclosure or "can" of the defibrillator also forms an electrode surface 42.

Although a variety of lead configurations can be used to pace the heart, to sense the intrinsic depolarizations of the heart and deliver defibrillation or cardioversion pulses, the present invention is disclosed in a configuration where ventricular pacing is delivered using the tip electrode 36 and the ring electrode 23 and sensing is accomplished using the tip electrode 36 and the can electrode 42. Defibrillation is accomplished using defibrillation electrode 40 and can electrode 42.

Figure 3:
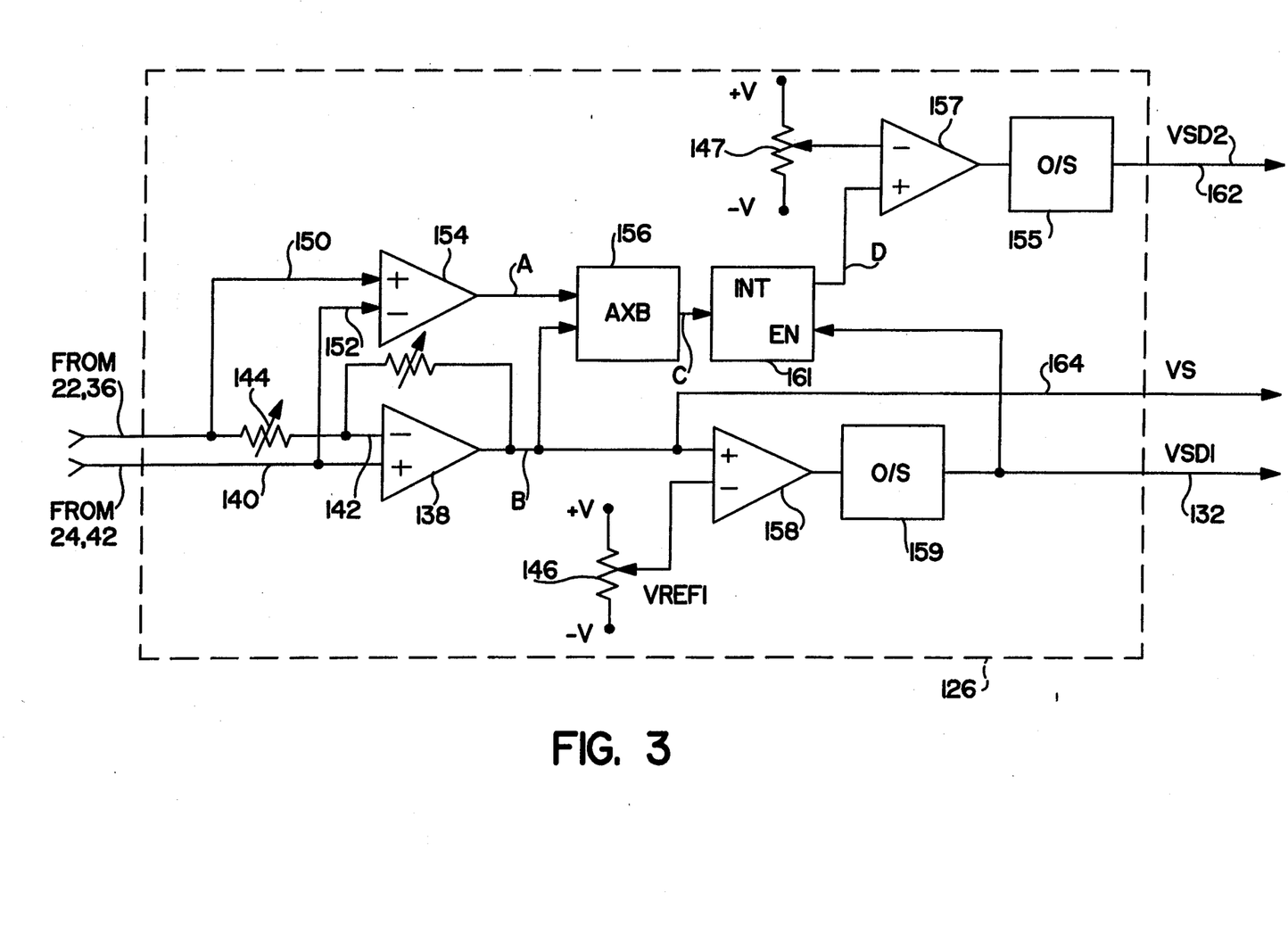
FIG. 3 is a block functional schematic diagram of a waveform discriminator according to the present invention.

FIG. 3 is a functional schematic diagram a preferred embodiment of the waveform discriminator of the present invention. The discriminator functions as a R-wave amplifier and detector, and includes amplifier circuitry more fully described in co-pending U.S. Pat. No. 5,156,149, issued to Hudrlik and in co-pending, allowed application Ser. No. 07/626,061, filed Dec. 12, 1990, for "Electronic Capture Detection for a Pacer", also by Hudrlik, both of which are incorporated by reference herein in their entireties. The active circuitry of the waveform discriminator 126 attempts to maintain an equilibrium condition between the sensing electrodes. The field perturbation caused by the passing wavefront is nulled out by the active circuitry which attempts to maintain a fixed relationship between the electrical potentials at the electrodes.

Current supplied to the electrodes in the attempt to maintain an electrode/electrolyte equilibrium condition is passed through a virtual load. The current delivered through the virtual load is monitored and forms the basis for the detection of the passing depolarization wavefront. It is possible to also monitor the voltage across the virtual load and multiply it with the current measurement to characterize the power delivered through the virtual load to the electrode system in response to the passing depolarization wavefront. The cardiac depolarization may be distinguished from noise based upon the power level of the depolarization signal. Further, the power level of the depolarization signal may be employed to distinguish between different types of depolarization waveforms. In the embodiments disclosed herein, the discriminator is employed to distinguish between normally conducted ventricular depolarizations and ectopic beats. Although this form of sense amplifier is disturbed both by the delivery of pacing energy to the lead system and by the recharge of the output capacitor, the system recovers very quickly, and thus requires blanking of its inputs only for a few milliseconds during and immediately following pulse delivery. However, if a greater degree of input blanking is desired it may be readily provided using conventional techniques.

The discriminator 126 includes an operational amplifier 138 which has its non-inverting input 40 connected to the can electrode (24, FIG. 1, 42, FIG. 2) of the implanted device. The inverting input 142 is coupled to the ventricular tip electrode (22, FIG. 1, 38, FIG. 2) through a variable resistor 144 which is used to set a virtual load resistance for the system. For purposes of waveform discrimination according to the present invention, this resistance may be set to match the source impedance of the heart and electrode system in combination, e.g. approximately 1000 to 2500 ohms. A feedback path is provided for the amplifier 138 by a resistance 148 which converts therethrough current to a voltage signal B, proportional thereto. In operation the op amp 138 provides a signal B which reflects the amount of current provided to the tip electrode (22 or 36) in the attempt to counteract the perturbation of the electric field surrounding the electrodes due to the passage of a depolarization wavefront.

Differential amplifier 154 is provided to measure the magnitude of the potential difference between the tip electrode (22 or 36) and the can electrode (24 or 42), by measuring the voltage across the virtual load resistance 144. The non-inverting input 150 of this differential amplifier 154 is coupled to the tip electrode (22 or 36), while the can electrode (24 or 42) is coupled to inverting input 152. The voltage output A of differential amplifier 154 is directly proportional to the voltage difference between the electrodes.

The voltage measurement A and the current measurement current B are used by multiplier 156 to provide a positive output signal C proportional to the instantaneous value of the power delivered through the virtual load resistance 144 in response to the passage of a cardiac depolarization wavefront. The instantaneous power signal is integrated over a time period following detection of the depolarization and the integrated signal is employed to discriminate between depolarization waveform types. Testing by the inventor has indicated that ectopic ventricular depolarizations produce a higher integrated power signal than normally conducted depolarizations. The current based signal B is employed to detect the occurrence of the depolarization.

Current signal B is provided to comparator 158, which compares the signal B to a threshold voltage VREF1 defined by voltage source 146. If the current signal B exceeds VREF, comparator 158 generates a positive output which triggers one-shot 159 to provide a V-sense detect signal VSD1 on line 132. The VSD1 signal may have a duration of 50–200 ms and defines the period over which the instantaneous power signal C is integrated by analog integrator 161. Current signal B is also provided to the VS output line 164, where it may be used, if desired, for digital signal analysis.

The output signal D of integrator 161 is provided to comparator 157 which compares the signal D to a threshold voltage VREF2 defined by voltage source 147. If the integrated power signal D exceeds VREF2, during the period defined by the VSD1 signal, comparator 157 generates a positive output which triggers one-shot 155 to provide a V-sense detect signal VSD2 on line 162. The duration of the VSD2 detect signal may be 1 ms or less, and indicates that the sensed beat was ectopic, rather than normally conducted.

The pacemaker, defibrillator or other device to which the discriminator is coupled can readily make use of the signals provided by the discriminator. The leading edge of the VSD1 signal may be employed to reset the timing of escape intervals in the context of a pacemaker and for measurement of R-R interval durations in the context of an anti-tachycardia device such as a pacemaker/cardioverter/defibrillator. The occurrence of a VSD2 signal may be employed to indicate that the sensed R-wave was ectopic, rather than normally conducted. This information may be employed to alter the operative parameters of the device.

In a pacemaker, operative parameters related to the sensing function may be altered. For example, in a DDD or VDD pacemaker, a longer post-ventricular atrial refractory period may be selected when ectopic beats are sensed. Alternatively, an operative parameter of the stimulating pulses such as their relative timing may be altered. For example, in a DDD or VDD pacemaker, the V-A escape interval following a sensed ectopic beat may be longer than the V-A escape interval following a normally conducted beat.

In the context of an antiarrhythmia device, the ectopic origin of the sensed beats may be employed to distinguish between various arrhythmia types, e.g. to distinguish between waveforms of ventricular origin associated with ventricular tachycardia and normally conducted ventricular waveforms associated with supraventricular tachycardias. This information may be employed to select the therapy to be delivered and to alter operative parameters of the therapies delivered. For example, timing of electrical pacing pulses may be altered in response to detection of ventricular tachycardia, in conjunction with termination of bradycardia pacing and initiation of tachycardia pacing. Similarly, the energy level of pulses applied to the heart may be increased in response to detection of ventricular tachycardia, in conjunction with termination of bradycardia pacing and delivery of a cardioversion pulse. In contrast, detection of supraventricular tachycardia may result in no therapy being delivered or in the device simply continuing to provide bradycardia pacing. If the present invention is employed to distinguish between other waveform types, e.g. fibrillation waveforms versus tachycardia waveforms, therapy types, pulse amplitudes and intervals associated with delivered therapies may also correspondingly be altered.

Figure 4:
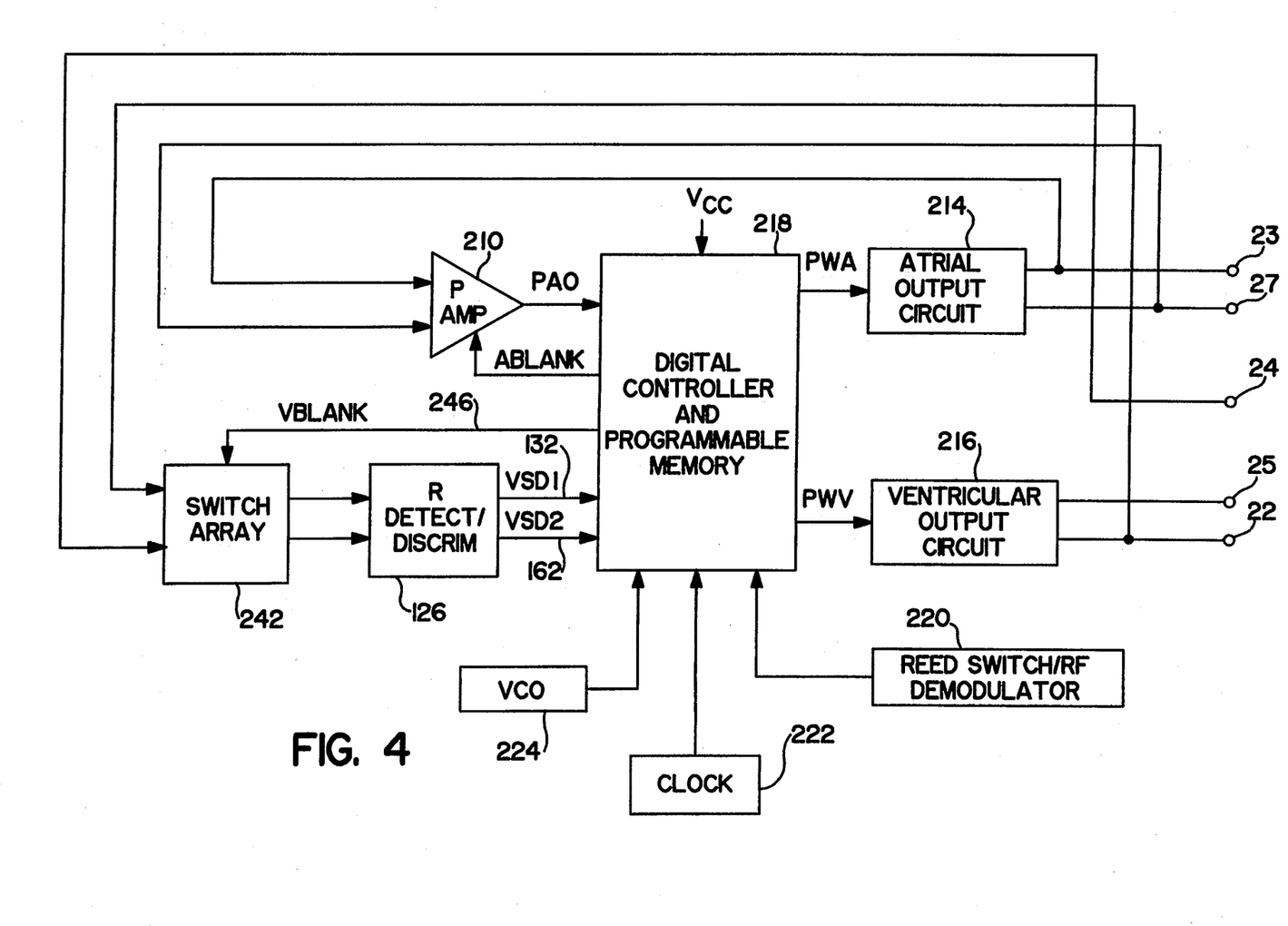
FIG. 4 is a functional block diagram depicting the interconnection of the waveform discriminator of FIG. 3 and the other circuitry of a prior art cardiac pacemaker.

FIG. 4 shows a general, functional diagram of a DDD type pacemaker in which the discriminator of the present invention has been employed. The general functional organization illustrated is known to the art, and serves as the backdrop for the present invention. The pacemaker is coupled to the heart by means of atrial electrodes 23 and 27, ventricular electrodes 22 and 25 and can electrode 24, each corresponding to the identically numbered electrodes in FIG. 1. Depolarizations of the atrium are sensed between electrode 23 and electrode 27. Depolarizations of the ventricle are sensed between electrode 22 and electrode 24.

Signals indicative of atrial depolarizations are sensed by P-wave amplifier 210, which generates output signals indicative of the detection of natural atrial contractions. Electrical signals indicative of ventricular contractions are sensed by R-wave discriminator 126, corresponding to the circuit illustrated in FIG. 3. Discriminator 126 generates output signals VSD1 and VSD2, indicative of normally conducted and ectopic ventricular depolarizations, as discussed above in conjunction with FIG. 3. Electrodes 22 and 34 are coupled to discriminator 126 via optional switch array 242 which serves to disconnect discriminator 126 from the electrodes during delivery of pacing pulses. Digital controller 118 provides a signal on VBLANK line 246, which controls switch array 242, preventing signals 126 during generation of atrial and ventricular pacing pulses.

In its commercial embodiments, a pacemaker according to the present invention will be typically controllable by means of an RF link between an external programmer and the implanted pacemaker. Adjustment of the parameters of digital controller 218 is accomplished by means of reed switch/RF demodulator 220, which functions generally as disclosed in U.S. Pat. No. 4,340,062, issued to Thompson, also incorporated herein by reference in its entirety. However, any programming/telemetry system according to prior art may be used to perform this function. VCO 24 and crystal clock 222 provide timing signals to digital controller 18. VCO 224 is preferably used to regulate the width of stimulation pulses such that the width of stimulation pulses increases as the battery voltage decreases.

Under control of digital controller 218, atrial output 214 provides stimulating pulses to the atrium of the heart via electrodes 23 and 27. Under control of digital controller 218, ventricular output circuit 216 similarly applies stimulating pulses to the ventricle of the heart by means of electrodes 22 and 25. Timing and control of sensing functions and of stimulating pulses, including heart chambers paced, heart chambers sensed, pulse intervals, amplitudes, refractory periods and pacing modes is provided by controller 218. These functions may correspond to any of the numerous prior art DDD type cardiac pacemakers, with the exception that the VSD2 signal may be employed as an alternate mechanism for identifying the occurrence of ectopic beats. The response of the pacer to detected ectopic beats may include a prolonged post-ventricular atrial refractory period as disclosed in U.S. Pat. No. 4,407,287, issued to Herpers et al, incorporated herein by reference in its entirety and optionally a prolonged V-A escape interval. Alternatively, the device may change its pacing mode from DDD mode to DVI mode for one cycle thereafter by temporarily disabling the atrial sensing function, as described in U.S. Pat. No. 4,590,944, issued to Mann et al, also incorporated herein by reference in its entirety.

Figure 5:
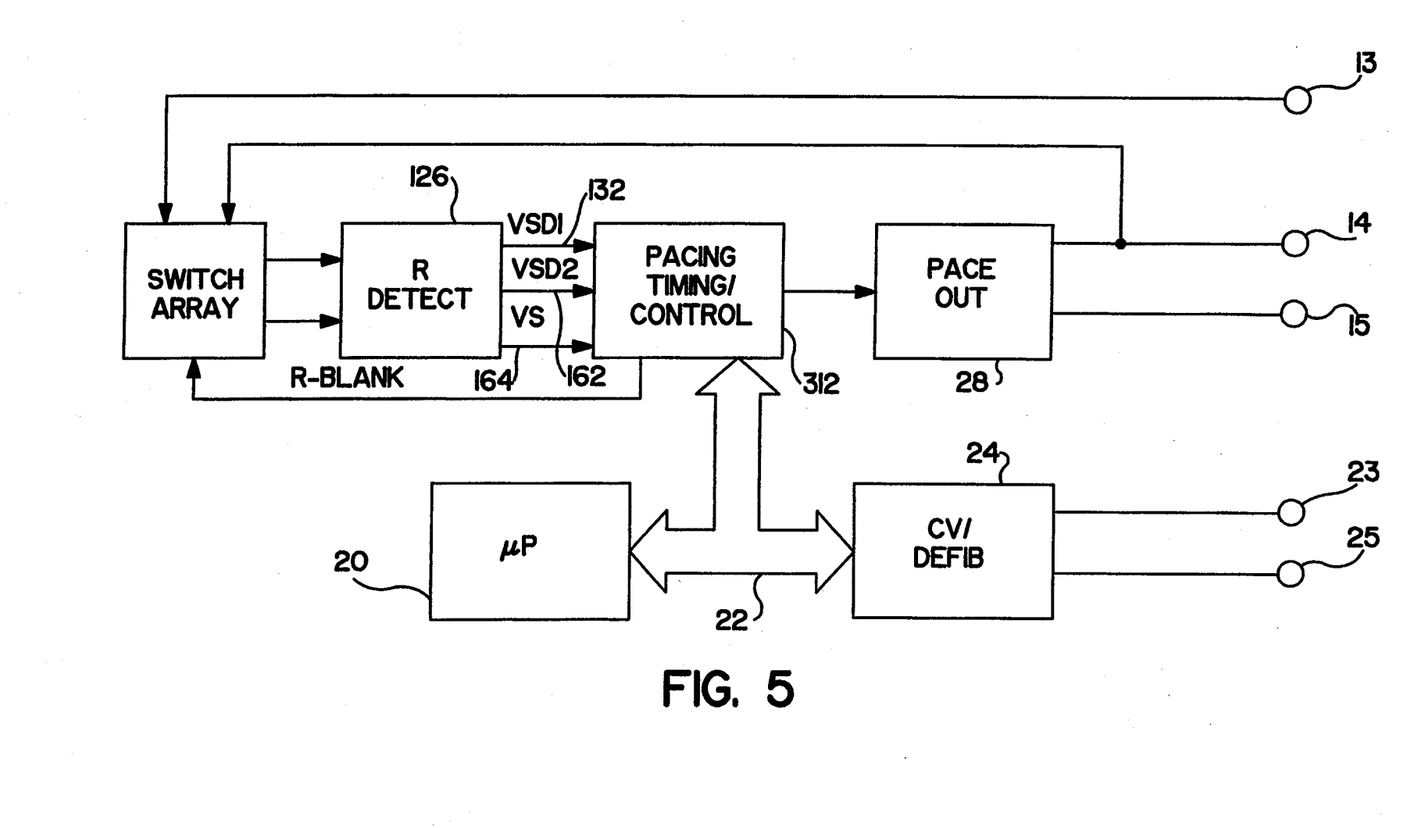
FIG. 5 is a functional block diagram depicting the interconnection of the waveform discriminator of FIG. 3 and the other circuitry of a prior art pacemaker/cardioverter/defibrillator.

FIG. 5 is a block, functional diagram illustrating the functional interrelation of the discriminator of the present invention in conjunction with a pacemaker/cardioverter/defibrillator. The present invention is believed practicable in the context of any implantable pacemaker/cardioverter/defibrillator, including devices as disclosed in U.S. Pat. No. 4,548,209, issued to Wielders, et al, U.S. Pat. No. 4,693,253, issued to Adams, U.S. Pat. No. 4,375,817, issued to Engle, et al, U.S. Pat. No. 4,384,585, issued to Zipes or U.S. Pat. No. 4,830,006, issued to Haluska, et al, all of which are incorporated herein by reference in their entireties.

In the illustrated embodiment, the microprocessor 320 controls the functions of the pacing circuitry 312 and the operation of cardioverter/defibrillator 324 by means of control/data bus 322. Pacer circuitry 312 includes a plurality of timers which operate under the control of microprocessor 320 to define blanking, refractory and V-V intervals and pulse widths for both VVI bradycardia pacing and anti-tachycardia pacing as well as sensing, timing and synchronization intervals for delivery of cardioversion and defibrillation pulses. Cardioverter/defibrillator 324 provides high energy defibrillation and cardioversion pulses to the heart by means of large surface area electrodes 40 and 42, corresponding to identically numbered electrodes illustrated in FIG. 2.

The discriminator 126, corresponding to the circuitry illustrated in FIG. 3, interfaces with the included cardiac pacemaker timing circuitry 312. As illustrated, the discriminator 126 is coupled to the heart by means of electrodes 36 and 42, corresponding to identically numbered electrodes in FIG. 2. The leading edge of the VSD1 signal is employed to reset the basic pacing interval (V-V interval) of the pacing circuitry 312. The occurrence of the VSD1 signal is also communicated to a microprocessor 320, by means of logic signals on control/data bus 322, where it is employed for measuring R-R intervals, for detection of tachyarrhythmias. VSD2 signals are also communicated to microprocessor 320 via control/data bus 322. The occurrence of a VSD2 signal indicates that the detected R-wave was of ectopic origin, which information may be employed by microprocessor 320 to distinguish between types of arrhythmias. For example, the waveform discrimination function of the present invention may be substituted for a measurement of R-wave width to discriminate between ventricular and supraventricular tachycardia, as disclosed in U.S. Pat. No. 5,193,535, issued to Bardy et al and incorporated herein by reference in its entirety. In the presence of a detected rapid heart rate, the occurrence of the VSD2 signals in conjunction with detected R-waves indicates the occurrence of a ventricular tachycardia. Correspondingly, the absence of VSD2 signals in conjunction with detected R-waves may indicate the occurrence of a sinus or other supraventricular tachycardia. If a ventricular tachycardia is identified, bradycardia pacing functions are temporarily terminated and antitachycardia pacing pulses or a higher energy cardioversion pulse may be delivered. If supraventricular tachycardia is identified, bradycardia pacing functions remain activated. The analog output signal B of op amp 138 (FIG. 1) is also communicated via VS line 164 through pacing circuitry 312 to control/data bus 322, allowing the microprocessor to perform any desired digital signal processing and/or ECG storage functions which may be desired.

Although the specification discloses the present invention as embodied in devices which sense ventricular depolarizations and deliver electrical pulses to the ventricles, it is believed that the invention is also of value in conjunction with devices which sense and/or treat the atrium, or other body tissues. Similarly, while two basic device architectures are disclosed above, it is believed that the present invention may be embodied in a device employing any of the numerous circuit and device architectures presently employed in electrical stimulators. As such, the above description should be understood as exemplary, rather than limiting, with regard to the scope of the claims which follow.

What is claimed is:

1. A cardiac pacemaker, comprising:
   pulse generator means for generating pacing pulses at predetermined intervals;
   means for sensing the occurrence of depolarizations of a heart chamber;
   means for producing signals indicative of power levels of sensed depolarizations of said heart chamber; and
   control means responsive to said signals for altering an operative parameter of said pulse generating means as a function of the power levels of said depolarizations.

2. A pacemaker according to claim 1 wherein said control means comprises means for altering a said predetermined interval.

3. A pacemaker according to claim 1 further comprising means for defining a power level threshold and wherein said control means comprises means for altering said operative parameter in response to said power level signal exceeding said power level threshold.

4. A pacemaker according to claim 1 or claim 3, wherein said means for producing signals indicative of power levels of sensed depolarizations of said heart chamber comprises:
   electrode means for electrically coupling to said heart chamber; means in response to said depolarizations to counteract depolarization induced changes in electrical potential adjacent said electrode means; and
   means for producing signals indicative of the power levels of said electrical current applied to said electrode means.

5. A pacemaker according to claim 4 wherein said means for producing signals indicative of the power levels of said electrical current applied to said electrode means comprises:
   means for producing current level signals indicative of the current levels provided by said charge providing means;
   means for producing voltage level signals indicative of the current levels provided by said charge providing means; and
   means for combining said voltage level signals and said current level signals to provide said power level indicative signals.

6. A pacemaker according to claim 5 further comprising means for defining a power level threshold and wherein said control means comprises means for altering said operating parameter in response to said power level signal exceeding said power level threshold.

7. A cardiac pacemaker, comprising:
   pulse generator means for generating pacing pulses at predetermined intervals;
   means for sensing the occurrence of depolarizations of a heart chamber;
   means for producing signals indicative of power levels of sensed depolarizations of said heart chamber; and
   control means responsive to said signals for altering an operative parameter of said sensing means as a function of the power levels of said depolarizations.

8. A pacemaker according to claim 7 further comprising means for defining a refractory period of said sensing means, and wherein said control means comprises means for altering a duration of said refractory period.

9. A pacemaker according to claim 8 wherein said sensing means comprises means for sensing atrial depolarizations and means for sensing ventricular depolarizations and wherein said means for defining said refractory period comprises means for defining a refractory period of said means for sensing atrial depolarizations.

10. A pacemaker according to claim 7 wherein said sensing means comprises means for sensing atrial depolarizations and means for sensing ventricular depolarizations and wherein said control means comprises means for disabling one of said atrial and ventricular sensing means.

11. A pacemaker according to claim 7 further comprising means for defining a power level threshold and wherein said control means comprises means for altering said operating parameter in response to said power level signal exceeding said power level threshold.

12. An antiarrhythmia stimulator, comprising:
   pulse generator means for generating electrical pulses at predetermined intervals;

means for sensing the occurrence of depolarizations of a heart chamber;

means for producing signals indicative of power levels of sensed depolarizations of said heart chamber; and control means responsive to said signals for altering an operative parameter of said pulse generating means as a function of the power levels of said depolarizations.

13. A stimulator according to claim 12 wherein said pulse generating means further comprising means for defining energy levels of said electrical pulses and wherein said control means comprises means for altering a said energy level.

14. A stimulator according to claim 12 wherein said pulse generating means further comprising means for triggering delivery of said electrical pulses at predetermined intervals and wherein said control means comprises means for altering a said predetermined interval.

15. A stimulator according to claim 12, comprising means for delivering first and second antiarrhythmia therapies to said patient's heart, and wherein said control means comprises means for selecting between said first and second therapies.

16. A stimulator according to claim 12 further comprising means for defining a power level threshold and wherein said control means comprises means for altering said operative parameter in response to said power level signal exceeding said power level threshold.

17. A stimulator according to claim 12, wherein said means for producing signals indicative of power levels of sensed depolarizations of said heart chamber comprises:

electrode means for electrically coupling to said heart chamber;

means for providing electrical charge to said electrode means in response to said depolarizations to counteract depolarization induced changes in electrical potential adjacent said electrode means; and means for producing signals indicative of the power levels of said electrical charge applied to said electrode means.

18. A stimulator according to claim 17 wherein said means for producing signals indicative of the power levels of said electrical charge applied to said electrode means comprises:

means for producing current level signals indicative of the current levels provided by said charge providing means;.

means for producing voltage level signals indicative of the current levels provided by said charge providing means; and means for combining said voltage level signals and said current level signals to provide said power level indicative signals.

19. A stimulator according to claim 18 further comprising means for defining a power level threshold and wherein said control means comprises means for altering said operative parameter in response to said power level signal exceeding said power level threshold.

20. Apparatus for producing signals indicative of power levels of sensed depolarizations of body tissue comprising:

electrode means for electrically coupling to said body tissue; means responsive to said depolarizations for counteracting depolarization induced changes in electrical potential adjacent said electrode means by providing electrical charge to said electrode means; and means for producing signals indicative of the power levels of said electrical charge applied to said electrode means.

21. Apparatus according to claim 20 wherein said means for producing signals indicative of the power levels of said electrical charge applied to said electrode means comprises:

means for producing current level signals indicative of the current levels provided by said charge providing means;

means for producing voltage level signals indicative of the current levels provided by said charge providing means; and means for combining said voltage level signals and said current level signals to provide said power level indicative signals.

22. Apparatus according to claim 21 wherein said charge providing means comprises a load impedance and means for providing said charge through said load impedance and wherein said means for producing current level signals comprises means for producing signals indicative of current levels through said load impedance and wherein said means for producing voltage level signals comprises means for producing signals indicative of voltage levels across said load impedance.

23. A stimulator according to claim 20 or claim 21 or claim 22 further comprising means for defining a power level threshold and means for generating an output signal in response to said power level signal exceeding said power level threshold.

* * * * *